United States Patent [19]

Jackson

[11] 4,125,569

[45] Nov. 14, 1978

[54] PROCESS FOR INCREASING HYDROGENATION RATE OF POLYMERIZED N-ALPHAOLEFINS

[75] Inventor: Steven M. Jackson, North Brunswick, N.J.

[73] Assignee: Mobil Oil Corporation, New York, N.Y.

[21] Appl. No.: 827,532

[22] Filed: Aug. 25, 1977

[51] Int. Cl.² .............................................. C07C 5/04
[52] U.S. Cl. .......................... 260/683.9; 260/676 R; 260/683.15 D; 260/677 H
[58] Field of Search ....................... 260/683.9, 677 H

[56] References Cited

U.S. PATENT DOCUMENTS

| | | | |
|---|---|---|---|
| 3,947,507 | 3/1976 | Isa et al. | 260/683.9 |
| 4,017,553 | 4/1977 | Cecsa et al. | 260/683.9 |
| 4,032,591 | 6/1977 | Cupples et al. | 260/683.9 |

*Primary Examiner*—Veronica O'Keefe
*Attorney, Agent, or Firm*—Charles A. Huggett; Raymond W. Barclay; Howard M. Flournoy

[57] ABSTRACT

Hydrogenation of polymerized olefins in the presence of alumina and a hydrogenation catalyst provides a greater hydrogenation rate than that obtained using the catalyst alone.

12 Claims, No Drawings

PROCESS FOR INCREASING HYDROGENATION RATE OF POLYMERIZED N-ALPHAOLEFINS

BACKGROUND OF THE INVENTION

1. Field of the Invention

This invention relates to a method of improving the rate at which polymerized olefins may be hydrogenated. It is more particularly concerned with increasing the hydrogenation rate of polymerized monoolefins, e.g., decene, which are useful as synthetic lubricants.

2. Description of the Prior Art

Alumina is well known for its usefulness in the sorption of undesirable gaseous and liquid materials from various organic media. In its calcined form it is also useful in certain catalytic processes. Alumina is also known to promote reactions with ammonia. Insofar as it is known it has never been used, particularly in unmodified form, to promote a hydrogenation reaction.

SUMMARY OF THE INVENTION

This invention is directed to a process for increasing the hydrogenation rate of polymerized normal alpha-olefins comprising hydrogenating said polymerized alpha-olefins under catalytic hydrogenation conditions in the presence of alumina and a suitable hydrogenation catalyst.

DESCRIPTION OF SPECIFIC EMBODIMENTS

The olefins particularly suitable for use herein are broadly termed alpha-monoolefins, e.g., 1-decene. In general, these so-called normal alpha-olefins may have between 6 and 12 carbon atoms per molecule. For example, 1-hexene, 1-octene, 1-nonene, 1-decene and 1-dodecene may be utilized after polymerization in the process embodied herein. The olefins may be substantially pure normal alpha-monoolefins, mixtures of olefins and/or paraffins containing substantial amounts of normal alpha-monoolefins. The mixtures of normal alpha-monoolefins desirably have between about 6 and about 12 carbon atoms with a mean value for the olefin chain length of about 10 carbon atoms. Thus, for example, a polymerized mixture of equal parts of 1-hexene, 1-octene, 1-decene and 1-dodecene can be utilized. However, mixtures having a mean chain length which is greater or less than 10 can also be advantageously used herein.

The normal alpha-monoolefins are usually polymerized either thermally or catalytically in the presence of a di-tertiary alkyl peroxide or a Friedel-Crafts catalyst. However, any other suitable polymerization process known to the art may be used. The preferred monomer is 1-decene which can be relatively pure monomer or an olefin or hydrocarbon mixture rich in 1-decene.

The hydrogenation catalyst is generally selected from the group consisting of metals selected from Group VIII and Group IB of the Periodic Table, various salts thereof and mixtures of said metals and/or said salts. For example, the metals can be Ni, Pd, Pt, Co, Cu, Ni—Cu (Alloy), Ni—Zn, Ni (carbonate, oxide, sulfate). Preferred as catalyst is nickel. However, any suitable hydrogenation catalyst known to the art may be used in the process disclosed and claimed herein. The hydrogenation catalysts are generally but not necessarily composited on a porous support, such as kieselguhr as for example nickel-on-kieselguhr. Other support materials include calcined (gamma) alumina, activated carbon, and silica-alumina extrudate. However, preferably the support materials should be porous, that is, have a porosity within about 100 $m^2/g$ and 400 $m^2/g$. The support itself is generally non-catalytic and substantially inert.

Uncalcined alumina monohydrate powder has proven most advantageous for use in the process embodied herein. The properties of a typical uncalcined alumina monohydrate so used are given in the table below.

TABLE I

| | |
|---|---|
| bulk density (lb/ft$^3$) | 18 |
| surface area (m$^2$/gm) | 300 |
| volume average particle size ($\mu$) | 13 |
| number average particle size ($\mu$) | 3.0 |
| pore volume (cc/gm) | 0.42 |

Other forms of alumina may also be used; these include calcined (gamma) alumina and uncalcined (spray dried) alumina fluid cracking catalyst.

The hydrogenation catalyst and the alumina are usually present in the reaction zone in a weight ratio of hydrogenation catalyst to alumina of from about 0.05–2 to about 1. Preferred weight ratio of the catalyst is from about 0.06 to about 0.6 to an alumina ratio of 1.

Conventional hydrogenation conditons known in the art are employed. For example, the hydrogenation temperature can vary from about 150° C to about 400° C, the pressure can vary from about 300 to about 500 psig. The hydrogenation depending, inter alia, upon temperature and pressure can take from about 0.1 of an hour to about 8 hours or more. Preferred reaction conditions are 175°–225° C, 450–500 psig and 0.15–1.0 hours.

The following examples are merely exemplary and are not as such limitations of this invention.

EXAMPLE 1

A continuous overflow reactor was used to prepare the polymer. Using 8 grams of aluminum chloride-methyl butyrate catalyst per 100 grams of 1-decene, polymer was synthesized at 55° C with a 4 hour residence time in the reactor. The reactor effluent was washed with water to remove the catalyst. The washed product thus obtained was topped at 10 mm. absolute pressure to remove unreacted 1-decene. The polymer had the properties set forth in Table II below.

TABLE II

| | Example 1 |
|---|---|
| K.V. at 100° C, cs | 38.19 |
| K.V. at 40° C, cs | 379.2 |
| V.I. | 149 |
| Pour Point, ° F | <−60 |
| Mol. Wt., Calc. | 1540 |

EXAMPLE 2

A 1180g. aliquot of the polymer of Example 1 was hydrogenated to saturate the olefinic double bonds. The hydrogenation was carried out in a suitable reaction vessel at a hydrogen pressure of 460 psig, a temperature of 200° C with nickel-on-kieselguhr catalyst (1.5 wt. %). After about 2.1 hours, 60% saturation of the polydecene was achieved.

EXAMPLE 3

The procedure and conditions of Example 2 were followed except that 1.0 wt. % alumina was added along with the catalyst to the reaction zone. An aliquot identical to that of Example 2 was used. After 0.2 hours, 60% saturation of the polydecene was obtained.

EXAMPLE 4

The procedure of Example 1 was followed except that the polymerization catalyst was boron triflouride and n-propanol. It had the properties set forth in Table III below.

TABLE III

|  | Example 4 |
|---|---|
| K.V. at 100° F, cs | 4.2 |
| K.V. at 40° F, cs | 26.9 |
| V.I. | 149 |
| Pour Point, °F | <−60 |
| Mol. Wt., calc. | 540 |

EXAMPLE 5

A 1180g. aliquot of the polymer of Example 4 was hydrogenated to saturate the olefinic double bonds. The hydrogenation was carried out in suitable reaction vessel at a hydrogenation pressure of 400 psig and a temperature of 200° C with nickel-on-kieselguhr catalyst (0.375 wt. %). About 80% saturation of the polydecene was achieved after about 1.75 hours.

EXAMPLE 6

The procedure and conditions of Example 5 were followed except that 2.5 wt. % of alumina was added along with the catalyst to the reaction zone. 80% polydecene saturation was achieved after 0.75 hours.

It is apparent from a comparison of the examples which utilized added alumina (Examples 3 and 6) and those which did not (Examples 2 and 5) during hydrogenation that the presence of alumina in the hydrogenation zone dramatically increases the rate at which the polymerized olefin was saturated.

Variations and modifications of the preferred embodiments described herein may be resorted to without departing from the spirit and scope of this invention as those skilled in the art will readily understand.

What is claimed is:

1. A process for increasing the hydrogenation rate of polymerized normal alpha-olefins or mixtures thereof having from about 6 to 12 carbon atoms per olefin comprising hydrogenating said polymerized alpha-olefins under catalytic hydrogenation conditions of from about 150°–400° C and from about 300–500 psig in the presence of added alumina, and a suitable hydrogenation catalyst in a weight ratio of catalyst to alumina of from about 0.05–2 to 1 and wherein the hydrogenation catalyst is selected from the group consisting of metals from Groups VIII and IB of the periodic Table, salts thereof and mixtures of said metals and or said salts.

2. The process of claim 1 wherein said alpha-olefin is a mixture of monoolefins having a mean chain length of about 10 carbon atoms.

3. The process of claim 1 wherein said normal alpha-monoolefin is 1-decene.

4. The process of claim 1 wherein said normal alpha-monoolefin is an equi-weight mixture of 1-hexene, 1-octene, 1-decene and 1-dodecene.

5. The process of claim 1 wherein the weight ratio of said catalyst to alumina is from about 0.06–0.6 to 1.

6. The process of claim 1 wherein the hydrogenation catalyst is nickel composited with a suitable support.

7. The process of claim 5 wherein the hydrogenation catalyst is nickel-on-kieselguhr.

8. The process of claim 1 wherein the hydrogenation is carried out at a temperature from about 175° to 225° C, a pressure of from about 450–500 psig for about 0.1 to about 8 hours.

9. In a process for the hydrogenation of polymerized alpha-monoolefins having between about 6 and about 12 carbon atoms the improvement wherein alumina is added to a hydrogenation catalyst in a weight ratio of alumina to catalyst of from about 1 to about 0.05–2 wherein said catalyst is selected from the group consisting of metals from Groups VIII and IB of the Periodic Table, salts thereof and mixtures of said metals and/or said salts.

10. The process of claim 9 wherein the alumina to catalyst weight ratio is from about 1 to about 0.06–0.6 to 1.

11. The process of claim 9 wherein the monoolefin is a mixture of monoolefins having between about 6 and about 12 carbon atoms.

12. The process of claim 9 wherein the monoolefins is an equi-weight mixture of 1-hexene, 1-octene, 1-decene and 1-dodecene and the catalyst is nickel-on-kieselguhr.

* * * * *